United States Patent [19]

Maccecchini

[11] Patent Number: 4,599,229

[45] Date of Patent: Jul. 8, 1986

[54] METHOD OF PROMOTING ANIMAL GROWTH USING ANTIBODIES AGAINST SOMATOSTATIN

[75] Inventor: Maria-Luisa Maccecchini, Northbrook, Ill.

[73] Assignee: International Minerals & Chemical Corp., Terre Haute, Ind.

[21] Appl. No.: 773,814

[22] Filed: Sep. 9, 1985

[51] Int. Cl.$^4$ .......................................... A61K 39/395
[52] U.S. Cl. .................................... 424/85; 435/68; 435/172.3; 435/172.2; 424/387
[58] Field of Search ...................... 260/112 B, 112 R; 424/85; 435/68, 172.3, 172.2

[56] References Cited

U.S. PATENT DOCUMENTS

| | | | |
|---|---|---|---|
| 4,172,124 | 10/1979 | Koprowski et al. | 435/172.2 X |
| 4,219,467 | 8/1980 | Pende et al. | 260/112 R |
| 4,363,877 | 12/1982 | Goodman et al. | 435/172.3 X |
| 4,366,246 | 12/1982 | Riggs | 435/68 |

FOREIGN PATENT DOCUMENTS 0016415  2/1981  Japan .................................... 424/85

OTHER PUBLICATIONS

Endocrinology, 106: 1027–1032 (1980), Varner et al.

*Primary Examiner*—Howard E. Schain
*Attorney, Agent, or Firm*—Thomas L. Farquer; Barbara G. Ernst

[57] ABSTRACT

A method of enhancing the growth rate of animals comprises passively immunizing them with growth-enhancing amounts of anti-somatostatin antibodies.

10 Claims, 2 Drawing Figures

METHOD OF PROMOTING ANIMAL GROWTH USING ANTIBODIES AGAINST SOMATOSTATIN

TECHNICAL FIELD

This invention relates to a method of enhancing the growth rate of animals. More specifically, this invention relates to enhancing animal growth rate by passively immunizing them with monoclonal or polyclonal antibodies against somatostatin.

BACKGROUND OF THE INVENTION

Somatostatin or somatotropin release-inhibiting factor is an antagonist of growth hormone releasing factor (GHRF) and is believed to interfere with growth by inhibiting growth hormone (GH) secretion.

Scientists have theorized that if somatostatin (S) does inhibit growth hormone secretion, manipulation of its levels may affect growth rate and body composition of animals bred for meat production. Literature reports of efforts to accomplish animal weight gain by auto-immunization, however, have been inconsistent. For example, Spencer and Williams reported auto-immunizing lambs with somatostatin linked to a carrier protein. The auto-immunized lambs gained weight more rapidly than did the control lambs; averaging 135% of the weight of the control lambs after nine weeks of treatment. Plasma somatomedin levels showed a five fold increase over the control levels; however, neither growth hormone levels nor insulin levels increased (*Animal Production* 32:376 (1981); *Veterinary Record*, p. 484, (May 22, 1984). In similar tests, Varner et al. reported that baseline and overall serum growth hormone concentrations were higher in anti-somatostatin (anti-S) auto-immunized lambs than in controls (*Endocrinology* 106:1027 (1980)). Despite this, Varner found that the immunized lambs gained significantly less weight than did control animals.

Thus, literature results on weight gain through active immunization are discrepant. It therefore is an object of this invention to develop a reproducible method for enhancing animal growth rates.

SUMMARY OF THE INVENTION

In accordance with the present invention, a method for enhancing the rate of growth in animals involves administering to the animals growth-enhancing amounts of anti-somatostatin monoclonal or polyclonal antibodies.

DETAILED DESCRIPTION OF THE INVENTION

Figure 1:
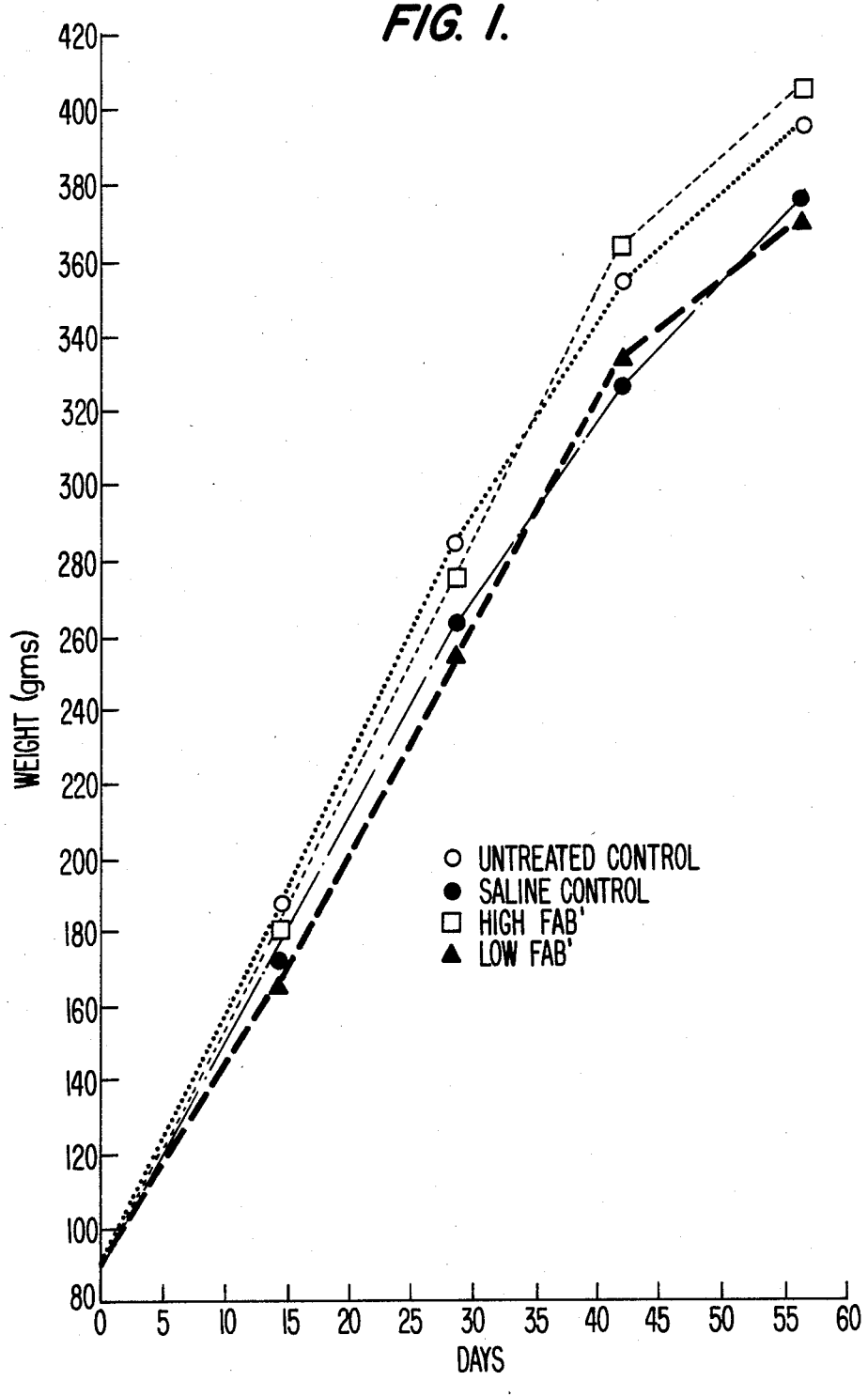
FIG. 1 is a graph illustrating the growth curve (mean weights) of rats which had been administered different amounts of heterologous antibody fragments specific for somatostatin.

The present invention relates to a method for enhancing the rate of growth in animals. More specifically, the invention relates to a method of enhancing growth rate by administering to the animals growth enhancing amounts of monoclonal or polyclonal antibodies specific for somatostatin obtained from the same species or different species of animal. As described in greater detail below, if homologous antibodies (i.e., antibodies derived from the same animal species as that to be treated) are used, either whole antibodies or antibody fragments may be administered. If the antibodies are obtained from a heterologous source (i.e., the antibodies are derived from a different animal species than the species being treated), preferably antibody fragments, rather than whole antibodies, are administered.

The antibodies used in the method of this invention are generally obtained using conventional techniques. Somatostatin is isolated, purified and coupled to a carrier protein. Typically, immunization of animals with an endogenous substance does not lead to antibody production against that substance. By coupling the endogenous protein, somatostatin in this instance, to an exogenous, carrier protein, a protein hybrid is formed which can be used as an antigen to elicit the desired immune response. A variety of carrier proteins can be linked to the somatostatin, including albumin, serum albumin, thyroglobulin, and δ-globulin.

Polyclonal antibodies may be obtained in accordance with conventional procedures. An animal, such as a rabbit, is infected a number of times over a period of, typically, a few weeks with the somatostatin-carrier protein hybrid. Blood samples containing the anti-somatostatin antibodies then are extracted from the animal.

The techniques for making monoclonal antibodies also are well known and are taught by U.S. Pat. No. 4,172,124 (1979), issued to Koprowski and incorporated herein by reference. Typically, the somatostatin and carrier protein are cross-linked with a cross-linker such as glutaraldehyde and injected intraperitoneally into an animal with immune response capability, preferably a mouse or a rat. Most of the antibodies formed are directed against the carrier protein; only a few are directed against the somatostatin. Spleenic lymphocytes are removed from the animals and screened for antibodies having a high specificity and affinity for somatostatin. The desired lymphocytes are suspended in a non-lethal medium.

Animal myeloma cells capable of being fused to lymphocytes from the injected animal then are mixed with the lymphocytes. The myeloma cells preferably are of the same species as the injected animal. The myeloma cells and lymphocytes are combined under cell-fusing conditions to produce the desired hybridomas.

The hybridoma cells are separated from unfused cells by placing the cell mixture in a medium which selectively kills the unfused myeloma cells and fused myeloma homokaryons but allows the hybridomas to survive. Standard commercial media can be used for this step. The unfused lymphocytes have a finite lifespan in vitro and naturally die, whereas the hybridoma cells reproduce indefinitely in a nutrient medium under cell growth conditions.

The monoclonal antibodies may be produced in vitro or in vivo using well-known methods. In vitro culturing of the hybridoma cells in a nutrient medium results in secretion of antibodies into the medium.

The supernatants of mature hybridoma cell cultures are tested for the presence of antibodies which selectively bind to somatostatin using conventional methods such as ELISA (enzyme linked immunosorbent assay). Cultures producing the desired antibodies are selected and subsequently cloned and characterized. The desired cell lines then may be cultured using conventional techniques. Samples may be frozen in liquid nitrogen for future use.

The anti-somatostatin animal antiserum can be purified by conventional means, such as ammonium sulfate precipitation and sepharose affinity chromatography. If desired, the purified anti-somatostatin immunoglobulins then can be digested with papain and the digest purified on a second column to yield anti-somatostatin Fab' fragments. If the animal from which the antibodies were obtained is of the same species as that which is to be immunized, either whole monoclonal or polyclonal antibodies or the Fab' fragments thereof may be administered. If, on the other hand, the antibodies are obtained from a heterologous animal species, it has been found that the Fab' fragments are more effective than the whole antibody in enhancing animal growth rate. It is theorized that when the whole heterologous antibody is administered to an animal, the antibody stimulates its own immune response and is inactivated. There is a much lower chance of this occurring when the animal is immunized with Fab' fragments.

The antibodies can be administered to animals in one of several ways. One easy and convenient method is to package a growth enhancing amount of the antibodies or antibody fragments into a slow-release delivery device and implant the device into the animal. The delivery device may be in the form of either a reservoir or a matrix system. Matrix and reservoir systems are well known in the art as implant devices and such systems comprising the antibodies useful in the method of this invention can be constructed in accordance with conventional techniques. The antibodies also can be administered by means of an infusion pump, such as those manufactured by Alza Corporation. Alternatively, the animals can be injected with a solution, such as a saline solution, containing a growth enhancing amount of the antibodies or antibody fragments.

The quantity of antibody preparation necessary to inhibit the action of somatostatin and, therefore, enhance growth rate varies with the animal species. One skilled in the art can readily determine optimum dosage ranges in target animal species by conducting standard dose titration experiments. For example, it has been found that a dose of approximately 10 to 20 μg of antibody per day is sufficient to lower somatostatin levels in 100-300 gram rats and show approximately 10-15% growth enhancement over other rats of similar weight which received saline injections.

The present invention is illustrated by the following example, which is not to be construed as limiting.

EXAMPLE

Growth Promoting Activity of Anti-S Fab' Fragments

Anti-somatostatin IgG antibodies derived from rabbits were obtained from Purification Engineering, Inc. The antibodies were digested by papain, and the digest repurified on an S-Sepharose 4B affinity column. A total of 5.4 mg anti-S Fab' fragments were obtained (135 ml. 40 μg/ml of Fab').

Eighty 3-week old Cox SD rats were randomly assigned to four treatment groups. One group was designated the untreated control, one group the saline control, one the high Fab' group and the fourth was designated the low Fab' group. These last 3 designations are defined below:

Saline control—injected control with 0.5 ml saline (0.9% NaCl)
high Fab'—20 μg/injection in 0.5 ml saline
low Fab'—200 ng/injection in 0.5 ml. saline After being quarantined for three days, intraperitoneal injections of 0.5 ml were given on days 1, 3 and 5 of each week for the duration of the 8 week study. Every two weeks one group of 5 animals from each of the 4 experimental conditions was weighed and sacrificed. Blood samples were taken and the sera were frozen and stored for future analysis. The bodies of the dead animals were inspected for unusual features.

The rats of each group were housed in a colony cage measuring 26"×20"×7" during the 8 week trial. The mean weights were taken at two-week intervals of all the rats present in each group. As noted above, in order to collect blood samples at each weighing date, five rats were sacrificed from each group every two weeks on the weighing day. Therefore, the number of rats represented by the mean varied from 20 rats at days 0 and 14 to 5 rats at day 56. All rats were fed standard laboratory rat chow and water, both ad lib. Lighting conditions were 16 hours of light and 8 hours of dark. The temperature fluctuated with ambient temperature (approximately 20° C.). Table A below shows the results of the mean weights. FIG. 1 shows the growth curve (mean weights) for the different groups. The percentage weight gain of the high Fab' group compared to the saline control group is listed in Table B below.

TABLE A

| | Mean Weight in Grams with Standard Deviation | | | |
|---|---|---|---|---|
| Days | Nontreated Control | Saline Control | High Fab' | Low Fab' |
| 0 | 87.9 ± 8.3 | 86.8 ± 7.9 | 89.5 ± 10.1 | 85.8 ± 8.4 |
| 14 | 177.5 ± 19.7 | 167.1 ± 23.7 | 181.3 ± 19.8 | 168.0 ± 20.9 |
| 28 | 279.3 ± 24.4 | 257.2 ± 31.5 | 267.0 ± 31.7* | 243.6 ± 29.9 |
| 42 | 350.3 ± 27.9 | 323.1 ± 31.9 | 362.1 ± 23.1* | 313.4 ± 26.2 |
| 56 | 394.0 ± 22.6 | 373.0 ± 17.5 | 403.4 ± 15.6* | 359.8 ± 23.2 |

*Differ significantly from saline control by a two-sided Dunnetts' test (Gill, J.L., Animal and Medical Sciences Bol. I, pp. 183-185 (1978) Iowa State University Press, Ames, Iowa), and by analysis of covariance (Steele, R.G.D. and Torrie, J.H., Principles and Procedures of Statistics, McGraw-Hill Book Co. Inc. N.Y. (1960) ch. 3, pp. 43-44, ch. 4, pp. 57-58 and ch. 5, pp. 67-76).

TABLE B

| Gain Improvement of Fab' Group Compared to Saline Control | |
|---|---|
| Day | % Gain of Fab' Group Compared to Saline Control |
| 0 | 102% |
| 14 | 107.3% |
| 28 | 105.7% |
| 42 | 111.2% |
| 56 | 109.6% |

Figure 2:
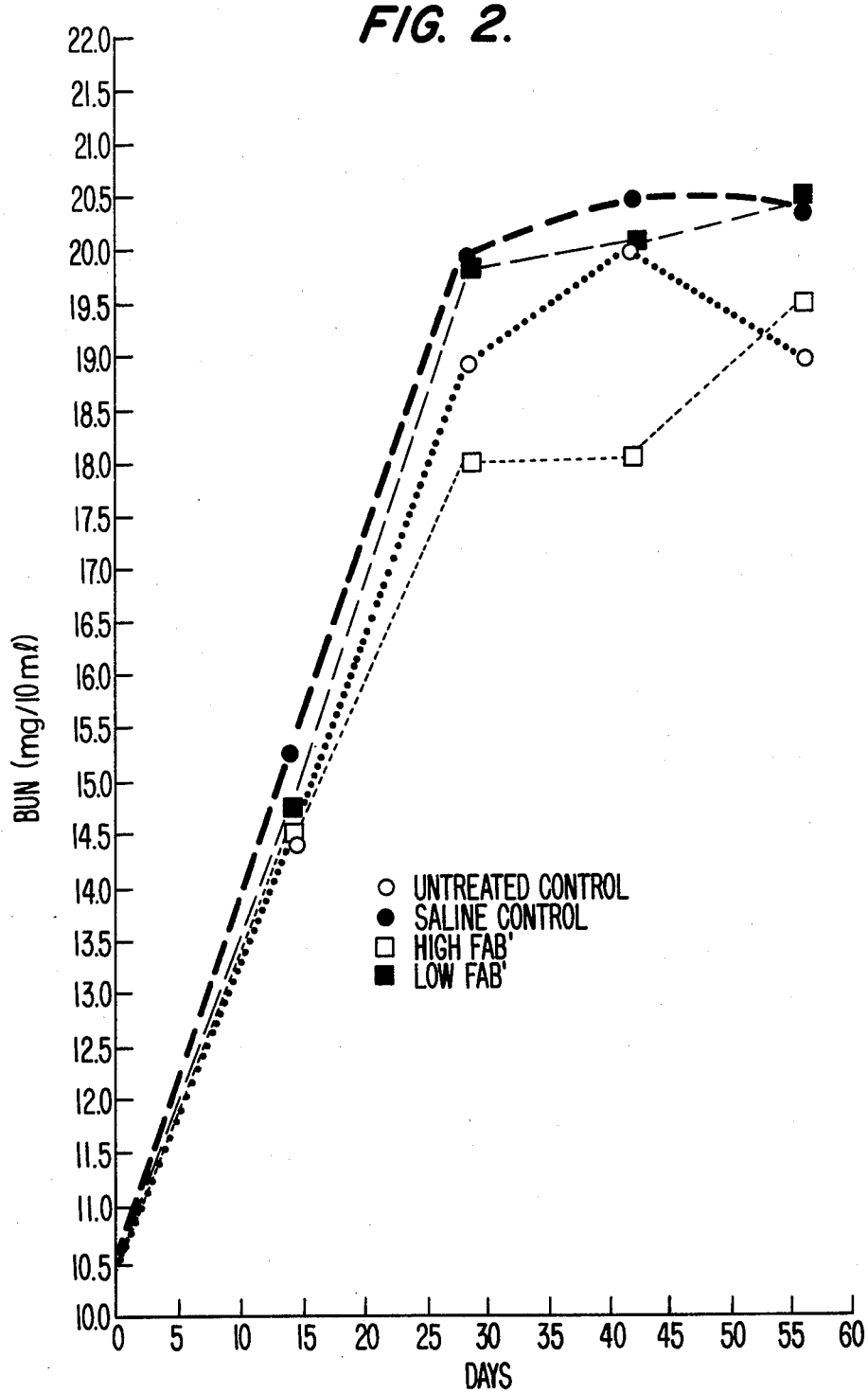
FIG. 2 is a graph illustrating changes in blood urea nitrogen levels of the same groups of rats during the period they were treated with the antibody fragments.

The levels of nitrogen excreted by an animal are a good indicator of anabolic activity. The levels of blood urea nitrogen (BUN) were measured to substantiate the weight gain results. FIG. 2 shows the mean blood ureanitrogen levels for the different groups. As shown in FIG. 2, the BUN levels measured in the experimental and control groups suported the weight data. The group injected with high Fab' fragments showed significantly lower BUN levels than the other groups.

In similar operations, an increased growth rate is achieved in various species of birds and mammals, when they are administered growth promoting amounts of monoclonal and polyclonal Fab' fragments and whole antibodies from homologous species and monoclonal and polyclonal Fab' fragments from heterologous species.

I claim:

1. A method of enhancing the rate of growth of an animal which comprises administering to said animal growth-enhancing amounts of antibodies against somatostatin.

2. The method of claim 1 wherein said antibodies are polyclonal antibodies.

3. The method of claim 1 wherein said antibodies are monolconal antibodies.

4. The method of claim 2 or 3 wherein the species of animal from which said antibodies are derived and the species of animal which will be administered said antibodies are homologous.

5. The method of claim 4 wherein whole antibodies are administered.

6. The method of claim 4 wherein Fab' fragments of said antibodies are administered.

7. The method of claim 2 or 3 wherein the species of animal from which said antibodies are derived and the species of animal which will be administered said antibodies are heterologous.

8. The method of claim 7 wherein Fab' fragments of said antibodies are administered.

9. The method of claim 1, 2 or 3 wherein the antibodies are administered by packaging a growth enhancing amount of the antibodies into slow-release delivery devices and implanting the devices in the animals to be immunized.

10. The method of claim 1, 2 or 3 wherein the antibodies are administered by injecting the animals with a solution comprising growth enhancing amounts of said antibodies.

* * * * *